United States Patent [19]

Soula et al.

[11] 4,216,171

[45] Aug. 5, 1980

[54] NOVEL COMPOSITIONS HAVING A BASE OF AMINOALKOXY AMINES

[75] Inventors: Gerard Soula, Meyzieu; Joël Le Ludec, Lyon, both of France

[73] Assignee: Rhone-Poulenc Industries, Paris, France

[21] Appl. No.: 957,925

[22] Filed: Nov. 6, 1978

[30] Foreign Application Priority Data

Nov. 21, 1977 [FR] France .............................. 77 34846

[51] Int. Cl.$^2$ ...................... C07C 89/00; C07C 93/04
[52] U.S. Cl. ................................................ 260/584 B
[58] Field of Search ..................................... 260/584 B

[56] References Cited

U.S. PATENT DOCUMENTS

| | | | |
|---|---|---|---|
| 1,923,178 | 8/1933 | Ulrich et al. | 260/584 B X |
| 2,813,877 | 11/1957 | Lambrech | 260/584 B X |
| 3,331,791 | 7/1967 | Cuscurida | 260/584 B X |
| 3,560,549 | 2/1971 | Poppelsdorf | 260/584 B X |
| 3,810,846 | 5/1974 | Atkinson | 260/584 B X |

FOREIGN PATENT DOCUMENTS 581994 10/1946 United Kingdom ................. 260/584 B

*Primary Examiner*—John Doll

[57] ABSTRACT

Compositions containing at least one aminoalkoxy amine of the formula:

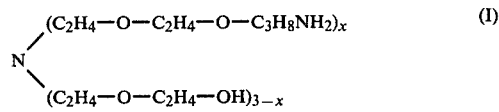

(I)

in which x is a whole number of from 1 to 3, are provided. They are prepared by cyanoethylation of tris(5-hydroxy-3-oxa-pentyl)amine with acrylonitrile followed by hydrogenation. They are useful as manufacturing intermediates, additives for lubricating oils, and in the synthesis of polyurethanes.

8 Claims, No Drawings

NOVEL COMPOSITIONS HAVING A BASE OF AMINOALKOXY AMINES

BACKGROUND OF THE INVENTION

Novel compositions having a base of aminoalkoxy amines are provided, as well as a novel process for preparing them.

The synthetic chemical industry is always desirous of obtaining novel chemical compounds and chemical intermediates for chemical synthesis and novel, improved methods for producing them. The present invention provides novel aminoalkoxy amines, as well as a novel and improved method for preparing them.

It is, accordingly, an object of the present invention to provide novel compositions having a base of aminoalkoxy amines.

It is a further object of the present invention to provide novel and improved processes for preparing the bases of aminoalkoxy amines of the invention.

Further objects will be apparent to those skilled in the art from the present description.

GENERAL DESCRIPTION OF THE INVENTION

The novel compositions having a base of aminoalkoxy amines which form the subject matter and an object of the present invention have the characteristic of containing at least one aminoalkoxy amine of Formula (I):

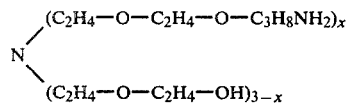

(I)

in which formula x is a whole number of from 1 to 3.

These novel compositions of the invention, having a base of aminoalkoxy amines, can be prepared by the novel process of the invention comprising cyanoethylation of tris(5-hydroxy-3-oxa-pentyl)amine of Formula (II):

(II)

with acrylonitrile in a molar ratio of acrylonitrile to amine of between about 1 and 4.5, followed by hydrogenation of the resultant nitriles of Formula (III):

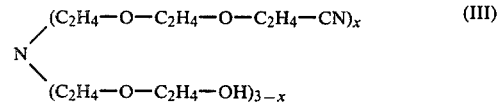

(III)

in which x is a whole number of from 1 to 3.

The ratio of acrylonitrile to amine employed is a function of the final composition which is desired. Thus, when the molar ratio of acrylonitrile to amine is greater than or equal to 3.5, tris(9-amino-3,6-dioxa-nonyl)amine can be selectively obtained. When the said molar ratio is less than 3.5, there will be obtained a composition which may contain the three products which satisfy Formula I, above, i.e., where x varies from 1 to 3.

The cyanoethylation of the tris(5-hydroxy-3-oxapentyl)amine can be carried out in accordance with the general methods described in the literature ("The Chemistry of Acrylonitrile," 2nd Edition, American Cyanamid Corp., New York (1958), page 24; H. A. Bruson, "Organic Reactions," 5, 79 (1949); and U.S. Pat. No. 2,326,721). It is customarily carried out in the presence of a basic catalyst, such as the alkali-metals, sodium and potassium, the oxides, hydroxides, alcoholates or amides of an alkaline-metal or quaternary ammonium bases such as trimethyl benzyl ammonium hydroxide. The quantity of alkaline or basic catalytic agent to be used varies from 0.1 and 5 percent referred to the weight of alkanolamine employed. In general, an amount of less than 1 percent is sufficient to produce the effect desired.

The cyanoethylation reaction is carried out at a temperature of between about 0° and 100° C., and preferably between about 30° and 50° C. This reaction may be carried out in the presence or absence of an organic solvent. As a solvent, there may be used, for example, benzene, dioxane, pyridine, and acetonitrile. The reaction can also be carried out in the presence of water.

Upon the introduction of the reagents, it is preferable to dissolve or disperse the catalyst in the alkanolamine, possibly diluted by the solvent, and to add the nitrile to the medium with agitation.

The cyanoethylation product previously obtained can be hydrogenated directly, or possibly after isolation, by any suitable means. Its reduction can be effected by the customary methods for the reduction of nitriles: Houben-Weyl, "Methoden der Organischen Chemie," 4th Edition, Vol. XI, p. 559 (1957). The method most commonly used is hydrogenation in the presence of nickel or cobalt catalysts, with the catalyst possibly deposited on a support. However, more particularly, recourse is had to the use of Raney nickel or Raney cobalt, employed in a proportion of 5 to 30 percent referred to the weight of the nitrile treated. It is advantageous to effect the hydrogenation with such catalysts in liquid ammonia or preferably in the presence of a base or basic agent in aqueous or organic medium. As basic agent, barium, sodium, potassium, or lithium hydroxides or quaternary ammonium hydroxides may be employed. The amount of base used, expressed with reference to the weight of nitrile treated, is about 1 to 30 percent.

The hydrogenation can take place in an inert organic solvent under the conditions of the reaction. There can be employed lower aliphatic alcohols, such as methanol, ethanol, propanol, isopropanol; diols, such as 1,2-ethanediol, 1,2-propanediol; ethers, such as ethyl ether, butyl ether, dimethoxy ethane, tetrahydrofuran and dioxan; partial ethers of polyhydroxy compounds, such as the monomethyl (or monoethyl) ether of ethylene glycol.

The hydrogenation reaction can be carried out at a temperature of between about 30° and 100° C., and preferably between about 60° and 80° C., under a hydrogen pressure of about 10 to 200 bars; in general, a pressure of about 20 to 30 bars is well suited for carrying out the hydrogenation.

In practice, the cyanoethylation product is added progressively to the suspension of catalyst maintained under the hydrogen pressure selected.

After the hydrogenation reaction, the catalyst is removed, the basic agent is neutralized, the solvent is eliminated, and the aminoalkoxy amines product can be distilled under the reduced pressure.

The tris(5-hydroxy-3-oxa-pentyl)amine of Formula II, above, employed to prepare the aminoalkoxy amines forming the object of the invention can be prepared by the method described in British Pat. No. 364,000 by action of ethylene oxide on a 20 percent ammonia solution. However, it is preferable to prepare this product of Formula II by condensation of an alkaline-metal (sodium or potassium) monoglycolate in solution in glycol on tris(2-chloroethyl)amine hydrochloride in a molar ratio of monoglycolate to hydrochloride equal to or greater than about 4; the condensation operation is carried out at the reflux temperature of the glycol (197° C.) for 2 to 6 hours using a glycolic solution containing from 0.5 to 5 mols of alkaline-metal monoglycolate, preferably 2 to 4 mols per liter of glycol. This latter method is disclosed in the present applicants' copending U.S. application entitled: "New Process for the Preparation of Tris(3-oxa-5-hydroxypentyl)amine, Ser. No. 957,926, filed Nov. 6, 1978."

The novel compositions forming the subject matter and an object of the invention can be used as manufacturing intermediates for additives, for lubricating oils, and as catalysts or cross-linking agents in the synthesis of polyurethanes.

SPECIFIC DESCRIPTION OF THE INVENTION

In order to disclose more clearly the nature of the present invention, the following examples illustrating the invention are given. It should be understood, however, that this is done solely by way of example and is intended neither to delineate the scope of the invention nor limit the ambit of the appended claims. In the examples which follow, and throughout the specification, the quantities of material are expressed in terms of parts by weight, unless otherwise specified.

EXAMPLE 1

Cyanoethylation 70.5 g. of tris(5-hydroxy-3-oxa-pentyl)amine (0.25 mol) and 0.46 ml. of caustic soda of 36° Baumé ($4.6 \times 10^{-3}$ mol) are introduced into a 250 ml. round-bottom flask provided with a mechanical agitator, a thermometer, a condenser and a dropping funnel. The mixture is heated to 38° C. and 53 g. of acrylonitrile (1 mol) are then introduced over the course of 1 hour.

At the end of the addition of the acrylonitrile, 0.6 ml. of HCl (d=1.19) is added in order to neutralize the sodium hydroxide. The sodium chloride precipitates. After filtration there is obtained an oil of straw yellow color consisting of tris(8-cyano-3,6-dioxa-octyl)amine.

Hydrogenation

The foregoing product is hydrogenated in an autoclave under a hydrogen pressure of 40 bars at 60° C. in the presence of 60 g. of Raney nickel suspended in 130 ml. of ethanol and of 0.75 ml. of caustic soda. The reaction takes place in 3 hours. After cooling, the autoclave is degasified and opened under at atmosphere of nitrogen. The contents are filtered. After removal of the catalyst, there are obtained 110 g. of oil, which correspond to a yield of 97 percent.

Elementary micro-analysis confirms that the product obtained is tris(9-amino-3,6-dioxa-nonyl)amine.

|  | Value Found % | Value Calculated % |
| --- | --- | --- |
| carbon | 55.32 | 55.75 |
| hydrogen | 10.68 | 10.62 |
| nitrogen | 12.5 | 12.39 |
| oxygen | 21.5 | 21.24 |

The product is obtained in a purity of 98 percent.

EXAMPLE 2

Cyanoethylation 70.5 g. of tris(5-hydroxy-3-oxa-pentyl)amine (0.25 mol) and 0.46 ml. of caustic soda of 36° Baumé ($4.6 \times 10^{-3}$ mol) are introduced into a 250 ml. round-bottom flask provided with a mechanical agitator, a thermometer, a condenser, and a dropping funnel. The mixture is heated to 38° C. and 42 g. of acrylonitrile (0.79 mol) are then introduced in the course of 1 hour. At the end of the addition of the acrylonitrile, 0.6 ml. of HCl (d=1.19) is added in order to neutralize the caustic soda. Sodium chloride precipitates. After filtration, to remove the sodium chloride, an oil of pale yellow color is obtained.

Hydrogenation 110.3 g. of the crude oil product produced above, dissolved in 110 ml. of absolute ethanol, are introduced into a 1-liter stainless steel autoclave provided with an agitation system and a hydrogen reserve of 250 ml., whereupon 56.9 g. of Raney nickel suspended in 130 ml. of ethanol and 0.75 ml. of caustic soda (36° Baumé, i.e., $4.8 \times 10^{-3}$ mol) are then added.

The autoclave is closed and purged three times with nitrogen (pressure=10 bars) whereupon the hydrogen is introduced. The pressure is increased to 40 bars at ambient temperature by means of the pressure reducer controlling the feed of hydrogen from the reserve. The mixture is heated to 60° C. The absorption of hydrogen ceases at the end of 2½ hours. After cooling, the autoclave is degasified and opened under an atmosphere of nitrogen.

The contents are then filtered and the catalyst washed with ethanol. After elimination of the ethanol from the combined filtrate and washings, a yellow oil is obtained.

There are obtained 105.4 g. of product, which corresponds to a yield of 93 percent.

The product is formed of:
85 percent of tris(9-amino-3,6-dioxa-nonyl)amine;
12 percent of bis-N,N(9-amino-3,6-dioxa-nonyl)-N-(5-hydroxy-3-oxa-pentyl)amine;
3 percent of bis-N,N(5-hydroxy-3-oxa-pentyl)-N-(9-amino-3,6-dioxa-nonyl)amine.

EXAMPLE 3

Cyanoethylation

The following reaction is carried out with the same apparatus as described in Examples 1 and 2:

0.46 ml. of caustic soda of 36° Baumé is added to 70.5 g. (0.25 mol) of tris(5-hydroxy-3-oxa-pentyl)amine. The mixture is heated to 38° C. and 20 g. of acrylontrile (0.375 mol) are then introduced in the course of 1 hour. At the end of the addition of the acrylonitrile, 0.6 ml. of HCl (d=1.19) is added in order to neutralize the caustic soda. Sodium chloride precipitates. After filtration, there is obtained an oil of straw yellow color having the following composition:
Residual triol: 10%
Dicyanoethylated triol: 40%
Monocyanoethylated triol: 40%
Tricyanoethylated triol: 10%

Hydrogenation

This mixture, produced above, is hydrogenated by the method described in the preceding example. The mixture is heated to 60° C. The absorption of hydrogen ceases at the end of 1½ hours. After cooling, the autoclave is degasified and opened under an atmosphere of nitrogen. The contents are filtered, whereupon the catalyst is washed with ethanol. After elimination of the ethanol from the combined filtrate and washings, flash distillation is effected at 210° C. under a pressure of 0.5 mm. of mercury in order to recover at the top the untransformed triol and at the bottom the mixture of aminoalkoxy amines, which is composed of:
- 44 percent of N,N-bis(5-hydroxy-3-oxa-pentyl)-N-(9-amino-3,6-dioxa-nonyl)amine;
- 44 percent of N-(5-hydroxy-3-oxa-pentyl)-N,N-bis(9-amino-3,6-dioxa-nonyl)amine;
- 12 percent of N,N,N-tris(9-amino-3,6-dioxa-nonyl)amine.

EXAMPLE 4

With the same apparatus as described in Examples 1 and 2, the following reaction is carried out:

0.46 ml. of caustic soda of 36° Baumé ($4.6 \times 10^{-3}$ mol) are added to 70.5 g. (0.25 mol) of tris(5-hydroxy-3-oxa-pentyl)amine. The mixture is heated to 38° C. and 24.6 g. of acrylonitrile (0.465 mol) are then introduced in the course of 2 hours. At the end of the addition of the acrylonitrile, 0.6 ml. of HCl (d=1.19) is added to neutralize the caustic soda. Sodium chloride precipitates. After filtration, the filtrate obtained is a yellow oil having the following composition:
- Residual triol: 4%
- Monocyanoethylated triol: 22%
- Dicyanoethylated triol: 58%
- Tricyanoethylated triol: 16%

This mixture is hydrogenated by the method described in Example 1. It is heated at 60° C. Under these conditions, the absorption of hydrogen ceases at the end of 2 hours. After cooling, the autoclave is degasified and opened under an atmosphere of nitrogen. The contents of the autoclave are filtered, and the catalyst washed with ethanol. After elimination of the ethanol from the combined filtrate and washings, flash distillation is effected at 210° C. under a pressure of 0.5 mm. of mercury in order to recover the untransformed triol at the top and the mixture of polyamines at the bottom. This mixture is analysed by gaseous-phase chromatography. It is composed of:
- 23 percent of N,N-bis(5-hydroxy-3-oxa-pentyl)-N-(9-amino-3,6-dioxa-nonyl)amine;
- 60 percent of N-(5-hydroxy-3-oxa-pentyl)-N,N-bis(9-amino-3,6-dioxa-nonyl)amine;
- 17 percent of N,N,N-tris(9-amino-3,6-dioxa-nonyl)amine.

PREPARATION OF STARTING MATERIAL

The tris(3-oxa-5-hydroxy-pentyl)amine used in the preceding examples for the preparation of the aminoalkoxy amines is prepared in the following manner:

Preparation of sodium glycolate 2200 g. (namely, 35.5 mols) of glycol and 218.5 g. (5.35 mols) of caustic soda in pellet form (98 percent) are introduced into a 3-liter round-bottom flask provided with a mechanical agitator, a thermometer, and a fractionation column followed by a condenser and a receiving flask.

The caustic soda is completely dissolved at 85° C. The greater part of the water (80 ml.) is collected by heating to 125° C. and the rest distilled with the glycol from 125° to 135° C. The solution thus obtained is cooled to 80° C.

Condensation with the tris(2-chloroethyl)amine hydrochloride 280.4 g. (namely, 1.16 mol) of tris(2-chloroethyl)amine hydrochloride, which can be prepared from triethanolamine hydrochloride by the method described for instance by K. Ward, JACS 57, 914 (1953), are added to the said solution of sodium glycolate in glycol. Heating is effected under reflux at 197° C. for 2 hours. Sodium chloride precipitates. A large portion of the glycol (1450 ml.) is then distilled under 3 mm. of mercury for 4½ hours.

The remaining material is then filtered. The cake of insoluble material is washed with 6 portions of 100 ml. each of acetone and then dried.

270 g. of sodium chloride are recovered as compared with a theoretical amount of 272 g.

The excess glycolate is neutralized with 0.7 mol (namely, 56.5 ml.) of hydrochloric acid (d=1.19). The acetone is evaporated and the oily residue obtained is distilled. The distillation middle-fraction (at between 210° and 220° C. at 2 mm. of mercury is collected. In this way, there are recovered 213 g. of a light yellow liquid formed of tris(5-hydroxy-3-oxa-pentyl)amine. The identity of this product was confirmed by infrared analysis, micro-analysis and nuclear magnetic resonance.

The terms and expressions which have been employed are used as terms of description and not of limitation, and there is no intention in the use of such terms and expressions of excluding any equivalents of the features shown and described or portions thereof, but it is recognzed that various modifications are possible within the scope of the invention claimed.

What is claimed is:

1. A composition having a base of aminoalkoxy amines comprising at least one aminoalkoxy amine of the formula:

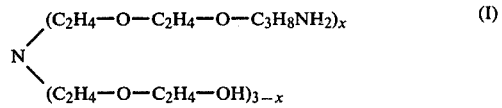

in which formula x is a whole number of from 1 to 3.

2. A composition according to claim 1 comprising tris(9-amino-3,6-dioxa-nonyl)amine.

3. A composition according to claim 1 comprising a mixture of tris(9-amino-3,6-dioxa-nonyl)amine; bis-N,N-(9-amino-3,6-dioxa-nonyl)-N-(5-hydroxy-3-oxa-penyl)amine; and bis-N,N-(5-hydroxy-3-oxa-pentyl)-N-(9-amino-3,6-dioxa-nonyl)amine.

4. A composition according to claim 1 comprising a mixture of about 85 percent of tris(9-amino-3,6-dioxa-nonyl)amine, about 12 percent of bis-N,N-(9-amino-3,6-dioxa-nonyl)-N-(5-hydroxy-3-oxa-pentyl)amine, and about 3 percent of bis-N,N-(5-hydroxy-3-oxa-pentyl)-N-(9-amino-3,6-dioxa-nonyl)amine.

5. A composition according to claim 1 comprising a mixture of N-(5-hydroxy-3-oxa-pentyl)amine-N,N-bis-(9-amino-3,6-dioxa-nonyl)amine; N,N-bis(5-hydroxy-3-oxa-pentyl)-N-(9-amino-3,6-dioxa-nonyl)amine; and N,N,N,-tris (9-amino-3,6-dioxa-nonyl)amine.

6. A composition according to claim 1 comprising a mixture of about 60 percent of N-(5-hydroxy-3-oxa-pentyl)amine-N,N-bis(9-amino,3,6-dioxa-nonyl)amine, about 23 percent of N,N-bis(5-hydroxy-3-oxa-pentyl)-N-(9-amino-3,6-dioxa-nonyl)amine, and about 17 percent of N,N,N-tris(9-amino-3,6-dioxa-nonyl)amine.

7. A composition according to claim 1 comprising a mixture of N,N-bis-(5-hydroxy-3-oxa-pentyl)-N-(9-amino-3,6-dioxa-nonyl)amine; N-(5-hydroxy-3-oxa-pentyl)-N,N-bis (9-amino-3,6-dioxa-nonyl)amine; and N,N,N,-tris(9-amino-3,6-dioxa-nonyl)amine.

8. A composition according to claim 1 comprising a mixture of about 44 percent of N,N-bis-(5-hydroxy-3-oxa-pentyl)-N-(9-amino-3,6-dioxa-nonyl)amine, about 44 percent of N-(5-hydroxy-3-oxa-pentyl)-N,N,-bis-(9-amino,3,6-dioxa-nonyl)amine, and about 12 percent of N,N,N-tris(9-amino-3,6-dioxa-nonyl)amine.

* * * * *